United States Patent [19]

Hayes

[11] 4,326,036
[45] Apr. 20, 1982

[54] PRODUCTION OF ETHANOL FROM SUGAR CANE

[76] Inventor: Frank W. Hayes, 144 Park West, London, W2 2QP, England

[21] Appl. No.: 197,538

[22] Filed: Oct. 16, 1980

[30] Foreign Application Priority Data

Oct. 17, 1979 [GB] United Kingdom ............... 36060/79

[51] Int. Cl.$^3$ .......................... C12P 7/06; C12P 7/14; C12P 7/08; C12P 19/02
[52] U.S. Cl. .................................. 435/161; 435/162; 435/163; 435/72
[58] Field of Search ............... 435/161, 162, 163, 164, 435/165, 105, 99

[56] References Cited

U.S. PATENT DOCUMENTS

| | | | |
|---|---|---|---|
| 2,222,885 | 3/1937 | Thomsen | 435/163 |
| 3,616,222 | 10/1971 | Dasinger | 435/105 |
| 3,990,944 | 11/1976 | Gauss et al. | 435/165 |
| 4,009,075 | 2/1977 | Hoge | 435/165 |
| 4,094,740 | 6/1978 | Lang | 435/165 |
| 4,220,721 | 9/1980 | Emert et al. | 435/161 |

OTHER PUBLICATIONS

Chemical and Engineering News, Sep. 16, 1974, p. 20.

*Primary Examiner*—Raymond N. Jones
*Assistant Examiner*—John E. Tarcza
*Attorney, Agent, or Firm*—Maky, Renner, Otto & Boisselle

[57] ABSTRACT

An integrated process is provided for producing ethanol from sugar cane. Harvested cane is chopped and shredded to provide a mass of fiber and juice which is digested in a first digester with a hemicellulase enzyme. Fibrous residue is separated by centrifuge and passed to a second digester for digestion with a mixed culture of a cellulase enzyme and an ethanol-producing culture. Fibrous residue from is pressed to provide a recycle juice extract and then burned to provide at least part of the heat energy requirement of the process. Juice extracts from digesters separated by centrifuges are combined, sterilized, flashed and passed to a fermentor for fermentation with an ethanol-producing microorganism. Ethanol is recovered from the process by separation utilizing a membrane.

8 Claims, 1 Drawing Figure

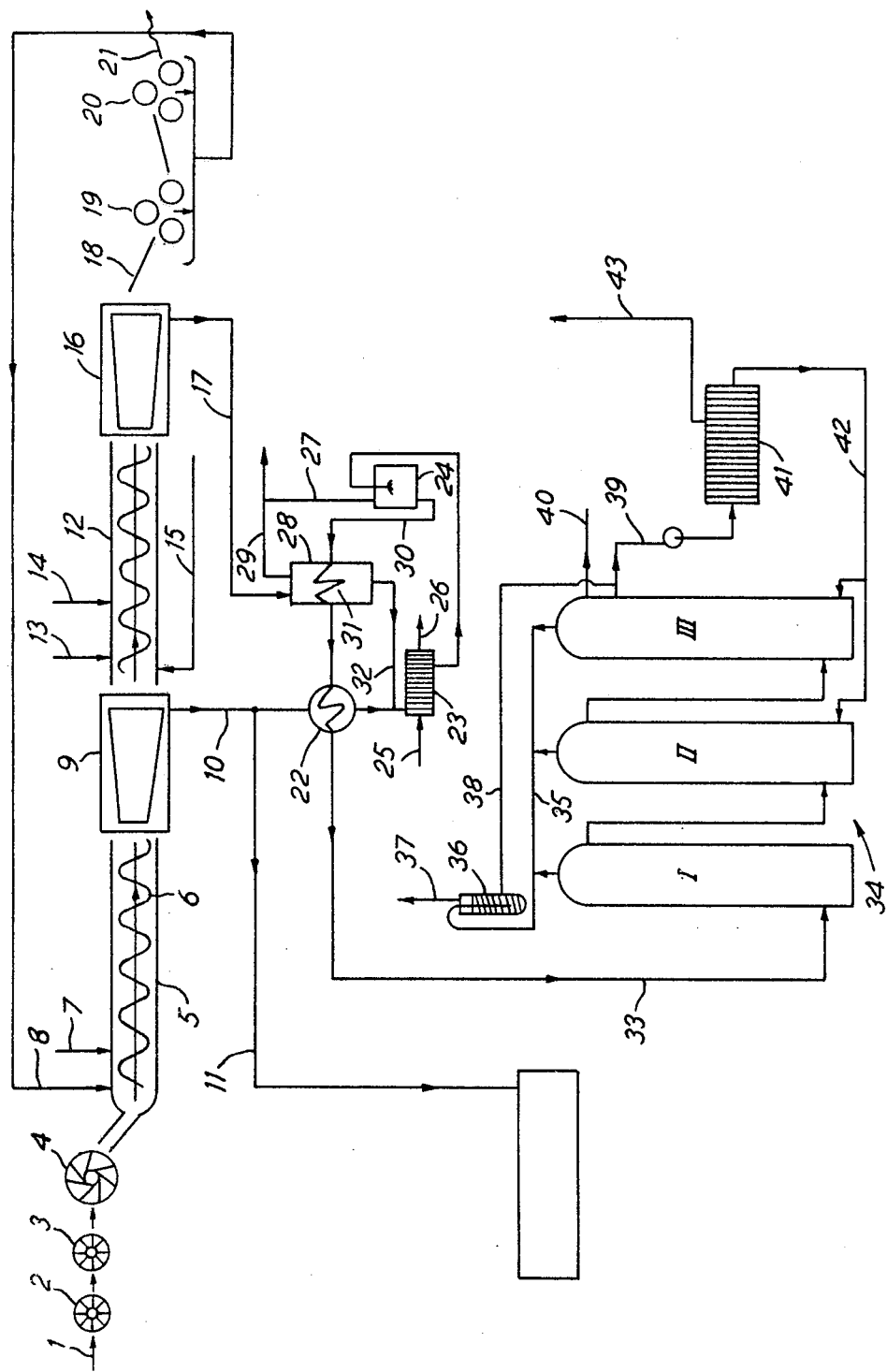

PRODUCTION OF ETHANOL FROM SUGAR CANE

This invention relates to the production of ethanol from sugar cane.

The production of ethanol from sugar cane molasses and juice is well known. Customarily in the production of ethanol from sugar cane the juice is first extracted from the cane by crushing or milling and then subjected to fermentation, with or without prior concentration of the juice by evaporation and/or crystallisation of sucrose. Substantial quantities of industrial alcohol are produced using molasses obtained as a residue in conventional sugar manufacturing processes. In the production of raw sugars from cane the economics are improved by using some or all of the fibrous residues, or bagasse, remaining after extraction of the juice from sugar cane, as a fuel to provide all or some of the heat required for the evaporation and crystallisation processes. However, the bagasse is potentially also a further source of fermentable sugar following saccharification or hydrolysis of the cellulose and/or hemicellulose content, and has indeed been used or proposed for this purpose. In U.S. Pat. No. 4,009,075 a three stage process is described for the production of alcohol from cellulosic material, the process comprising (i) steam sterilisation of cellulosic raw material, e.g. cellulosic waste, (ii) concurrent digestion and fermentation of the sterilised cellulose using a mixed culture comprising a cellulase enzyme and a yeast, and (iii) stripping of the product alcohol, e.g. by vacuum distillation, and recycle of the cellulase enzyme and the yeast. Advantages of the process are said to be the elimination of large volumes of cooling water otherwise needed to control the temperature of fermentation; substantially complete reaction since the continuous removal of the products forces the reactions through to completion, and easy recycle of the bottoms product to the fermentor to provide the enzyme and yeasts for the fermentation of fresh, sterilised feed. The advantage of vacuum distillation of product alcohol during the fermentation process is also discussed in Chemical and Engineering News, Sept. 16, 1974, page 20 which discloses a new development in the industrial production of ethanol from high concentration sugar solutions, e.g. molasses solutions containing up to 50% sugar.

The production of soluble sugars from cellulosic material e.g. bagasse is also disclosed in U.S. Pat. No. 3,616,222. In this process bagasse is simultaneously or sequentially treated with a mixed culture comprising a first organism e.g. *Trichoderma viride* which randomly attacks the cellulose molecule at intermediate points to shorten the chain length, but without producing soluble sugars, and a second organism, e.g. *Aspergillus fumigatus* which attack the cellulose molecule from the ends to produce soluble sugars. Improved yields of sugar are said to be obtained.

World demand for industrial alcohol is escalating, not least because of its utility as a fuel or fuel supplement, e.g. in admixture with gasoline, and because of its availability from a renewable source. One such source, of great potential, particularly in developing countries is sugar cane and a need exists for a truly economic process for the conversion of sugar cane into alcohol, and moreover one which can be easily carried out within the technological and economic conditions prevailing in the producer country.

According to the present invention, ethanol is produced from sugar cane economically and in bulk and at high purity by a process which involves total utilisation of the sugar cane, partly as a fuel to provide the heat requirements of the process, but mainly as a source of fermentable material.

According to the invention, harvested sugar cane with or without the foliage, but generally without, the foliage being customarily burned off in situ in known manner prior to harvesting of the cane, is first chopped and shredded to provide a digestion mass of juice and fibre. In a first continuous digestion stage the digestion mass is subjected to the hydrolytic action of hemicellulase-producing organisms and/or isolated hemicellulase enzymes to break down at least some of the hemicellulose content of the cane into fermentable sugars, e.g. pentoses.

Following the first digestion, the fibrous residue is separated from excess liquid, for example, by passage through a continuously operating centrifuge, and the liquid containing mainly sucrose, glucose and fructose from the original cane juice, pentoses produced by the hemicellulase digestion, and some initial fermentation products produced in a manner to be described, are passed to fermentation, whilst the fibre residue is passed to a second continuous digestion stage. In the second stage digestion, the fibre residue is subjected to the combined action of a cellulase enzyme (or whole cells of the organism) and an ethanol-producing fermentation culture, preferably a thermophilic organism, to break down a limited portion of the cellulose content of the fibre and initiate fermentation of the resulting glucose.

Following the second digestion, the fibrous residue is separated from the excess liquid, for example, by passage through a second continuously running centrifuge, and the liquid, containing glucose, fructose, some residual sucrose from the original cane and some initial fermentation products, is passed to fermentation proper in admixture with the liquid separated from the first digestion stage.

The fibrous residue or bagasse from the second digestion stage, the amount of which can be closely controlled by varying the reaction time intensity in digestion stages one and two, is now passed to a bagasse-burning boiler plant to provide at least some and preferably all the heat requirement of the process. Because of the high moisture content of the fibrous residue from the second centrifugal liquid extraction stage, this residue may be passed through a three-roller mill to obtain a further liquid extract which can be recycled to the first digestion stage, before the remaining fibrous residue ('bagasse') is passed to combustion.

An important point is that the organisms used in the digestion stages, as a mixed culture, work in symbiosis, with an enhanced effect as compared with the same organisms in single culture.

A significant feature of the process of this invention, as so far described, is the double digestion of the sugar cane fibre, which not only contributes to the amount of fermentable material recovered from the cane, but enables complete utilisation of the cane with close tailoring of the amount of bagasse passed to the boilers to the total heat energy requirements of the process, which in any case are lower than in normal raw sugar manufacture due to the fact that fermentation is performed on the juices as extracted, without evaporation and concentration. It is this combination of features which contributes significantly to the economic success of the present invention.

Following extraction the two liquid extracts are combined, sterilised and fermented using a continuous fermentation technique, and incorporating membrane separation of the product ethanol as formed.

The process of the present invention, in a particularly preferred form, will now be described with reference to the accompanying drawing, which illustrates a flow sheet for the preferred process.

Referring to the flow sheet, topped and harvested sugar cane is fed via line 1 to two rotating knife choppers 2, 3 operating in series to chop the cane into short lengths e.g. up to 10 cms. From there the chopped cane is fed to a swinging hammer mill, or shredder 4, or to two such mills or shredders operating in series, which operate to reduce the cane to a finely shredded condition. At this stage there is no separation of juice which is substantially completely absorbed by the shredded cane to provide a moist spongy fibre mass which passes to the first digester 5. Digester 5 operates on a continuous basis at ambient temperature with the fibre mass being fed therethrough at a controlled, but variable rate, depending on the desired throughput for the entire plant. Digester 5 consists essentially of a horizontal tubular reactor through which the contents are advanced by a rotating helical screw conveyor 6 axially positioned within the reactor.

To the digester 5 is added via line 7 a hemicellulase, or a culture which produces hemicellulases, plus any additional nutrients necessary for the organism to effect hydrolytic cleavage of at least part of the hemicellulose content of the fibre into the constituent pentoses. Also introduced into the digester 5 via recycle line 8 is a recycle stream containing fermentable sugars and some initial fermentation products expressed from the bagasse in a final milling stage prior to burning and which is to be described subsequently.

From the digester 5 the total digestion mass of fibre and liquid containing in solution sucrose, glucose, fructose and pentoses, the latter from the hydrolytic action of the hemicellulase, plus some sugars and initial fermentation product from the recycle stream, is fed to a centrifuge 9, which is a continuously running solids-discharging centrifuge, for the separation of the solution from the fibrous residue. From the centrifuge 9 the solution is passed to a fermentor (to be described) via line 10, optionally with the recovery of a slip stream via line 11 for the recovery of pentosans and pentoses as a by product of the process.

Following the flow path of the partially digested fibre mass, this is discharged from the centrifuge 9 into a second digester 12 similar in construction to the digester 5. Introduced to the second digester 12 via lines 13 and 14 respectively are a cellulase enzyme or a culture containing cellulase-producing organisms and an ethanol forming culture plus any additional nutrients necessary to achieve hydrolytic cleavage of at least some of the cellulose content of the fibre to glucose by the action of the cellulase enzyme and conversion of at least some of the glucose (and any other fermentable sugars which will also be present) to initial fermentation products including ethanol. The combined action of a cellulase enzyme and an ethanol producing fermentation culture in the second digester is believed to promote breakdown of the cellulose content of the fibre to yield fermentable sugars and thus increase the overall yield of the process. The digester 12 is preferably operated at a moderately elevated temperature, e.g. 60°–70° C., using a thermophilic ethanol producing culture. Additional liquid, e.g. steam condensate, may be added to the digester 12 via line 15 both to provide additional fluid for the hydrolytic and fermentation process and for temperature control. From the second digester 12, the digestion mass is passed to a second centrifuge 16, preferably again a continuously running, discharging centrifuge, for the separation of a second stage extraction solution via line 17, and a second stage fibrous residue or bagasse via line 18. From centrifuge 16, the bagasse is fed to a three-roller mill, or pair of mills 19, 20 operating in series and serving to extract remaining moisture from the bagasse. The extract containing water, sucrose, glucose, other fermentable sugars, initial fermentation products including ethanol, as well as residual amounts of the cellulose enzyme and fermentation culture provides a recycle stream which is fed via line 8 back to the first digester 5. It will be evident from this that in addition to the reaction already discussed, namely enzymic hydrolysis of hemicellulose by the hemicellulase, other reactions may or may not take place in the first digester 5, including some possible hydrolytic splitting of the cellulose by virtue of recycled cellulase enzymes, and some fermentation of glucose and other fermentable sugars by virtue of recycled fermentation organisms. Insofar as such reactions serve to remove by further reaction the products of an earlier hydrolytic process, which is essentially an equilibrium reaction, such additional reactions are beneficial in promoting the hydrolysis reactions and hence the yield of fermentable sugars in the first stage extraction solution.

Generally the second centrifuge 16 and the three-roller mill or mills will co-operate to provide a final bagasse containing about 50% of moisture, which is satisfactory for subsequent combustion. From the mills the final bagasse is passed via line 21 to the combustion chamber of a boiler plant (not shown) which provides all the heat requirements of the process. The boiler plant should generate steam at high pressure (minimum 27.2 atm.) and temperature and this steam should be fed to 'back-pressure', or 'pass-out' turbines, generating electricity and providing process steam at, say, 2–5 atm., for process use such as sterilisation and distillation. Preferably, the amount of bagasse passed to combustion, which will in large measure be controlled by the duration of the two digestion stages, will be such as to provide exactly for the whole heat energy input for the process, this balance contributing to a highly economic process for the production of ethanol from sugar cane without further energy input.

From the centrifuge 9, the first stage extraction juice is fed via a heat exchanger 22 through a plate-type sterilizer 23 to a flash chamber 24. In the sterilizer, the juice is heat-sterilized by indirect heat exchange contact with steam fed via line 25 and vented as condensate via line 26. To conserve energy, the condensate may be fed to the second digester as the temperature control and fluidising medium via line 15, any excess passing to boiler feed. From the flash chamber 24 ethanol vapour is taken off via line 27 and passed to an ethanol distillation system not shown, together with ethanol vapour recovered from a second flash chamber 28 via line 29. The feed to the second flash chamber 28 comprises the second stage extraction juice taken from centrifuge 16 via line 17 to the second flash chamber. As shown, the second flash chamber is heated by passage therethrough of the liquid bottoms product from the first flash chamber 24 fed via line 30 through a coil 31 in the second flash chamber 28. Further heat is recovered from the bottom product of the first flash chamber 24 by passage through the heat exchanger 22 in indirect heat exchange relation with the first stage extraction solution in line 10.

The bottoms product of the second flash chamber 28 is fed via line 32 and combined with the first stage extraction solution in line 10 following passage through the heat exchanger 22 and prior to passage through the sterilizer 23.

From the heat exchanger 22 the combined liquid stream is fed via line 33 to a continuous three-stage fermentation unit 34, into which an ethanol-producing fermentation culture inoculum is introduced, along with any additional nutrients necessary to support the growth of the culture. In the continuous fermentation unit stage I embraces the growth phase of the microorganism under mildly aerobic conditions whilst in stage II the medium and growth characteristics of the microorganism are adapted to anaerobic conditions conducive to the optimum production of ethanol in stage III. From each of the three stages $CO_2$ gas is led via line 35 to a gas-liquid separator 36, the separated $CO_2$ gas being vented via line 37 either to atmosphere or to a $CO_2$ liquefaction plant, and the liquid returned via line 38 to the ethanol product line 39 from the third stage of the fermentation unit. Typically the fermentation will be carried out using an adapted thermophilic strain of a known ethanol producing microorganism capable of working under the anaerobic conditions in stage III at above ambient temperatures.

In stage III a side-stream of the fermenting broth is pumped via line 39 through the membrane separator 41 where the ethanol is removed from the downstream side of the membrane by pervaporation and the product-ethanol vapour is taken by line 43 to the distillation and rectification unit for final product recovery.

The continuous removal of the enthanol as formed in the final stage fermenter overcomes the well-known inhibiting effect of high ethanol concentrations on the fermentation organism. From the membrane separator 41 the stripped fermentation product stream is recycled to stages II and III of the fermentation unit via line 42.

From stage III the fermented wash passes by line 40 for further treatment to recover product ethanol entrained therein and to recover a dried fermentation wash valuable as an animal feed.

It will thus be seen that the invention provides a totally integrated process for the production of ethanol from sugar cane in an efficient and highly economic manner. The hemicellulase and cellulase enzymes to be used in digesters 5 and 12 and the ethanol-producing microorganism to be used in conjunction with the cellulase enzyme in the second digestion stage, as well as in the final fermentation stage, will be a matter of choice and suitable enzymes and enzyme sources will be apparent to those skilled in the art, the present invention residing in the integrated process for the production of ethanol from sugar cane, rather than in the particular organisms or combinations of organisms used. However, as a guide, suitable hemicellulase and cellulase enzymes may be selected from *trichoderma viride, aspergillus wentii, thielaviopsis paradoxa,* and *thielatia terrestris* including mutants and strains thereof, whilst suitable ethanol-producing organisms include *saccharomyces cerevisiae, saccharomyces uvarum, thermoactinomyces sp., zymomonas* and *bacillus stearothermophilus* and mutants and strains thereof, and especially thermophilic strains thereof. Extra cellular enzyme preparations may also be used.

Instead of producing ethanol, the process of the present invention can readily be adapted to the production of other solvents and solvent mixtures from sugar cane, and other sugar sources, by the substitution of appropriate microorganisms at the fermentation stage, and also at the second digestion stage. For example, the process of the present invention is readily adapted to the production of a solvent mixture of butanol/acetone/ethanol by substitution of a bacterium such as *C. acetobutylicum* or a thermophilic derivative thereof, in place of the ethanol-producing culture.

I claim:

1. A method for the production of ethanol from sugar cane which comprises:
   (i) chopping and shredding the harvested sugar cane to provide a digestion mass of juice and fibre;
   (ii) subjecting the digestion mass of juice and fibre in a first continuous digestion zone to the hydrolytic action of a hemicellulase enzyme to break down at least some of the hemicellulose content of the sugar cane fibres into fermentable sugar;
   (iii) separating the product digestion mass produced in step (ii) into a liquid fraction containing fermentable sugars both from the original juice and produced in the digestion zone by said enzyme, and a fibrous residue fraction;
   (iv) subjecting the fibrous residue fraction from step (iii) in a second continuous digestion zone to the combined action of a cellulase enzyme and an ethanol-producing fermentation culture, thereby to partially break down the cellulose content of the fibre residue into a fermentable sugar and to initiate fermentation of that fermentable sugar, and any residual fermentable sugar carried over from the first digestion zone;
   (v) separating the product digestion mass produced in step (iv) into a second liquid fraction comprising a partially fermented sugar juice, and a fibrous residue;
   (vi) combining the liquid fraction from step (iii) with the liquid fraction from step (v) and subjecting the combined liquid fractions in a fermentation zone to a fermentation process using an ethanol-producing microorganism thereby to produce ethanol;
   (vii) recovering the ethanol produced in step (vi); and
   (viii) burning at least part of the fibrous residue produced in step (v) to provide at least some of the heat energy requirements of the process.

2. A method according to claim 1, wherein the amount of fibrous residue burnt in step (viii) is sufficient to provide substantially the whole of the heat energy requirement of the process.

3. A method according to claim 1, wherein, prior to burning, the fibrous residue from step (v) is pressed to extract a juice therefrom, and wherein said juice is recycled to the first digestion zone.

4. A method according to claim 1, wherein the first digestion zone is operated at ambient temperature and the second digestion zone is operated at elevated temperature utilising a thermophilic ethanol-producing culture.

5. A method according to claim 1, wherein, in step (vii), the product ethanol is recovered from the fermentation product of step (vi) by membrane separation, and the fermentation residue after separation of the product ethanol is recycled to the fermentation zone.

6. A method according to claim 1, wherein the liquid fraction from step (iii) and/or the liquid fraction from step (v) are flashed prior to fermentation to recover therefrom an initial stream of product ethanol.

7. A method for the production of ethanol from sugar cane which comprises:
  (i) chopping and shredding the harvested sugar cane to provide a digestion mass of juice fibre;
  (ii) subjecting the digestion mass of juice and fibre in a first continuous digestion zone to the hydrolytic action of a hemicellulase enzyme to break down at least some of the hemicellulose content of the sugar cane fibres into fermentable sugar;
  (iii) separating the product digestion mass produced in step (ii) into a liquid fraction containing fermentable sugars both from the original juice and produced in the digestion zone by said enzyme, and a fibrous residue fraction;
  (iv) subjecting the fibrous residue fraction from step (iii) in a second continuous digestion zone to the combined action of a cellulase enzyme and an ethanol-producing fermentation culture, thereby to partially break down the cellulose content of the fibre residue into a fermentable sugar and to initiate fermentation of that fermentable sugar, and any residual fermentable sugar carried over from the first digestion zone;
  (v) separating the product digestion mass produced in step (iv) into a second liquid fraction comprising a partially fermented sugar juice, and a fibrous residue;
  (vi) pressing the fibrous residue from step (v) to extract a juice therefrom;
  (vii) recycling the juice extracted in step (vi) to the first digestion zone;
  (viii) combining the liquid fraction from step (iii) with the liquid fraction from step (v) and subjecting the combined liquid fractions in a fermentation zone to a fermentation process using an ethanol-producing microorganism thereby to produce product ethanol;
  (ix) recovering the ethanol produced in step (viii); and
  (x) burning an amount of the fibrous residue produced in step (v) sufficient to provide substantially the whole of the heat energy requirements of the process.

8. A method according to claim 7, wherein the first digestion zone is operated at ambient temperature and the second digestion zone is operated at elevated temperature utilising a thermophilic ethanol-producing culture.

* * * * *